United States Patent [19]
Kessel et al.

[11] Patent Number: 6,143,929
[45] Date of Patent: Nov. 7, 2000

[54] PROCESS FOR PREPARING GUANIDINE DERIVATIVES

[75] Inventors: Knut Kessel, Mannheim; Michael Kluge, Ludwigshafen; Thomas Greindl; Thomas Bogenstätter, both of Bad Dürkheim; Günter Scherr, Ludwigshafen; Matthias Rauls, Limburgerhof; Richard van Gelder, Ludwigshafen, all of Germany

[73] Assignee: BASF Aktiengesellschaft, Ludwigshafen, Germany

[21] Appl. No.: 09/459,582

[22] Filed: Dec. 13, 1999

[30] Foreign Application Priority Data

Dec. 23, 1998 [DE] Germany ............... 198 60 048

[51] Int. Cl.⁷ .................................................. C07C 229/26
[52] U.S. Cl. ............................................................ 562/560
[58] Field of Search ............................................. 562/560

[56] References Cited

U.S. PATENT DOCUMENTS 5,719,319  2/1998  Weiss et al. .

FOREIGN PATENT DOCUMENTS

| | | |
|---|---|---|
| 1518852 | 6/1973 | Germany . |
| 3812208 | 10/1989 | Germany . |
| 0 915 083 A2 | 5/1999 | Germany . |
| 53-077 364 | 7/1978 | Japan . |
| 53-077364 | 7/1978 | Japan . |
| 55-004 349 | 12/1980 | Japan . |

OTHER PUBLICATIONS

Fearing et al. "Some Strongly Basic Derivatives of (+)– and (–)–1–Hydrosy–2–aminobutane[1]" JACS, vol. 76, Sep. 5, 1954, pp. 4382–4385.

Schwetlick et la., "Organikum " 1977, VEB Deutscher Verlang der Wissenschaften XP–002133400 pp. 44–46.

Kirk–Othmer Encyclopedia of Chemical Technology, 4th ed., (1993), vol. 7, John Wiley & Sons, NY, pp. 692–695 and 721, 1993.

*Primary Examiner*—Johann Richter
*Assistant Examiner*—Brian J. Davis
*Attorney, Agent, or Firm*—Keil & Weinkauf

[57] ABSTRACT

A process for preparing guanidine derivatives, in particular creatine, is described and entails an O-alkylisourea salt and a primary or secondary amine being reacted in the presence of crystals of a guanidine derivative.

10 Claims, No Drawings

PROCESS FOR PREPARING GUANIDINE DERIVATIVES

The present invention relates to a process for preparing guanidine derivatives of the formula I

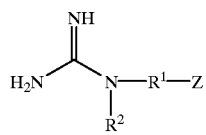
(I)

in which
- $R^1$ is $C_1$–$C_8$-alkylene or a divalent cycloaliphatic radical with 5 to 10 carbon atoms
- $R^2$ is $H_1$–$C_8$-alkyl, or
- $R^1$ and $R^2$ represent, together with the N atom to which they are bonded, a 5- or 6-membered Z-substituted ring,
- Z is $COOR^3$, $SO_2OR^3$ or $PO(OR^3)(OR^4)$,
- $R^3$ is in each case independently H, an alkali metal or an equivalent of an alkaline earth metal and
- $R^4$ is in each case independently H, an alkali metal, an equivalent of an alkaline earth metal or $C_1$–$C_6$-alkyl, by reacting an O-alkylisourea salt of the formula II

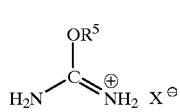
(II)

in which
- $R^5$ is $C_1$–$C_8$-alkyl and $X^\ominus$ is an equivalent of an anion, with an amine of the formula III

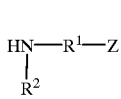
(III)

in which
$R^1$, $R^2$ and Z have the stated meanings.

The invention relates in particular to a process for preparing creatine from an O-alkylisourea salt and sarcosinate.

Guanidine compounds of the formula I are widespread in nature. Important representatives of this class of substances are, for example, compounds such as arginine and creatine. Creatine occurs in vertebrate muscle tissue, in particular as creatine phosphate, and plays an important part as energy carrier in the cell. Creatine is increasingly being used as dietary supplement to enhance physical performance. Creatine is also used for treating disturbances of muscle function characterized by increased creatine excretion in the urine.

EP-A 0754679 describes a process for preparing creatine or creatine monohydrate from cyanamide and sodium or potassium sarcosinate in water or a mixture of water and an organic solvent. A disadvantage of this process is the use of aqueous solutions of pure cyanamide. These solutions are very costly and, because of the instability of cyanamide, generally not widely available.

DE-A 38 12 208 discloses a process for preparing 4-guanidinomethylcyclohexanecarboxylic acid, in which 4-aminomethylcyclohexanecarboxylic acid is reacted with an O-alkylisourea derivative in a polar protic solvent.

JP-A 53/077364 describes a process for preparing creatine, in which an O-alkylisourea salt is gradually added to an aqueous sarcosine solution which is kept constantly in the pH range from 10 to 12. However, this process has certain disadvantages which make it appear unsuitable for industrial preparation of creatine. Thus, it has been found that the reaction mixture becomes increasingly viscous and more difficult to stir as conversion increases. The resulting creatine monohydrate moreover has a purity of only 97%. in addition, the resulting product has a very broad particle size distribution with a very low average particle size. This leads to the filterability of the product being inadequate. The large fine material fraction obtained after drying is undesirable because of the dusting of the product during packaging and transferring between containers. Although the product can be purified, and the particle size adjusted, for example by recrystallization, the additional process step is extremely costly because of the low solubility of creatine and is associated with large losses of product because of the low temperature dependence of the solubility of creatine.

It is an object of the present invention to develop the process mentioned at the outset further so that crystalline guanidine derivatives of the formula I are obtained in a simple manner, in high purity and high yield and with a narrow particle size distribution; it is additionally intended that it be possible to adjust the particle size so that easily filterable crystal suspensions are obtained.

We have found that this object is achieved by reacting the O-alkylisourea salt of the formula II with the amine of the formula III in the presence of seed crystals of the guanidine derivative of the formula I. Seed crystals are present throughout the reaction. The reaction preferably takes place in the presence of from 1 to 40% by weight, in particular 2 to 35% by weight, particularly preferably 5 to 20% by weight, based on the reaction mixture, of seed crystals. The stated values apply to the batchwise procedure and to the continuous procedure after the stationary state has been reached. In the latter case, smaller amounts of seed crystals, e.g. about 0.1% by weight, are also sufficient for starting up.

The applicant has found in wide-ranging tests that in the process of JP-A 53/077364 the concentration of creatine in the reaction mixture exceeds the saturation concentration 5-fold at times because the system is prone to formation of a metastable supersaturated phase, and crystallization is kinetically inhibited. The consequence of this is that spontaneous formation of crystal nuclei starts at very high supersaturations. Moreover there is simultaneous formation of many crystal nuclei so that a product with a high proportion of small particles is obtained. In addition, on spontaneous crystallization from supersaturated solution impurities from the reaction medium become involved.

The novel process avoids these disadvantages by the O-alkylisourea of the formula II and amine of the formula III being brought into contact and reacted in the presence of crystals of guanidine derivative of the formula I, which act as seed crystals for product deposition. It is possible in this way to keep the supersaturation of the reaction mixture in guanidine derivative of the formula I below a value at which spontaneous formation of crystal nuclei starts. In addition, because the proportion of guanidine derivative of the formula I present in solution is smaller owing to the presence of the seed crystals, its hydrolysis is suppressed by the reaction medium which is usually strongly basic.

The novel process makes use of an O-alkylisourea salt of the formula II. A preferred possibility for preparing O-alkylisourea salts consists of reacting urea with alkylating agents such as dialkyl sulfates.

The O-alkylisourea salt is expediently obtained by a process in which urea and an alkyl group-transferring reagent are reacted in a continuously operated reactor at a temperature of 40–200° C. It is moreover possible and advantageous to recycle a part-stream of the O-alkylisourea salt which results in oily form to dissolve the urea employed. The recycled O-alkylisourea salt additionally acts as catalyst for the alkylation reaction and as diluent which limits the temperature rise in the exothermic reaction and prevents thermal decomposition of the thermolabile O-alkylisourea salt formed. A particularly suitable continuously operated reactor for reacting urea and alkyl group-transferring reagents, e.g. dimethyl sulfate, is a tubular reactor.

Alternatively, O-alkylisoureas can be obtained by reacting anhydrous cyanamide with alcohols in the presence of acids.

$R^5$ in the formula II is branched or unbranched $C_1$–$C_8$-alkyl, in particular methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl. $C_1$–$C_4$-Alkyl is preferred, such as methyl, ethyl, propyl, isopropyl, butyl, with methyl being particularly preferred.

X in formula II is an equivalent of an anion such as a halide, e.g. $Cl^-$, $Br^-$, $I^-$, or a $C_1$–$C_8$-alkyl sulfate, e.g. methyl sulfate or ethyl sulfate, sulfate, hydrogen sulfate. O-Methylisourea methyl sulfate is most preferred.

The other starting material employed is an amine of the formula III. $R^1$ is a branched or unbranched $C_1$–$C_8$-alkylene radical, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 2,2-dimethylpropylene, 1-methylpentylene, 2-methylpentylene, 3-methylpentylene, 4-methylpentylene, 1,1-dimethylbutylene, 1,2-dimethylbutylene, 1,3-dimethylbutylene, 2,2-dimethylbutylene, 2,3-dimethylbutylene, 3,3-dimethylbutylene, 1-ethylbutylene, 2-ethylbutylene, 1,1,2-trimethylpropylene, 1,2,2-trimethylpropylene, 1-ethyl-1-methylpropylene, 1-ethyl-2-methylpropylene, n-heptylene, n-octylene; or a divalent cycloaliphatic radical having 5 to 10 carbon atoms, such as 1,2-, 1,3-, 1,4-cyclohexylene, 1,2- or 1,3-cyclopentylene or radicals of the following structure:

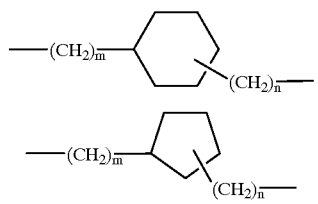

in which n and m may assume the values 0, 1 or 2, with the proviso that n and/or m are different from 0. In the cycloaliphatic radicals, both cis and trans configurations are possible.

$C_1$–$C_4$-Alkylene is preferred, such as methylene and ethylene.

The radical $R^1$ may be substituted by one or more, e.g. 1 to 3, substituents selected from an optionally protected amino, hydroxyl or cyano group.

$R^2$ is H or $C_1$–$C_8$-alkyl, preferably H, methyl or ethyl.

Alternatively, $R^1$ and $R^2$ may represent, together with the N atom to which they are bonded, a 5- or 6-membered Z-substituted ring, e.g. a piperidine or pyrrolidine ring.

Z is $COOR^3$, $SO_2OR^3$, or $PO(OR^3)(OR^4)$, in which $R^3$ is in each case independently H, an alkali metal such as sodium or potassium, or an equivalent of an alkaline earth metal such as calcium, and $R^4$ is in each case independently H, an alkali metal, an equivalent of an alkaline earth metal or $C_1$–$C_6$-alkyl.

The amine of the formula III is preferably an amino carboxylic acid, amino sulfonic acid or amino phosphonic acid or a salt thereof. Particular preference is given to sarcosine, in particular in the form of sodium or potassium sarcosinate, and glycine, taurine or 4-aminomethylcyclohexanecarboxylic acid.

According to the invention, the O-alkylisourea salt of the formula II and the amine of the formula III are brought into contact in the presence of seed crystals of the guanidine derivative of the formula I. Thus, it is possible, for example, for the O-alkylisourea salt, preferably in the form of an aqueous solution, to be mixed with the seed crystals, and for the resulting suspension to be reacted with the amine of the formula III, preferably in the form of an aqueous solution. On the other hand, the amine of the formula III can be mixed with the seed crystals and then be mixed with the O-alkylisourea salt. In a further alternative, the O-alkylisourea salt of the formula II and the amine of the formula III can be added to the seed crystals as powder or in the form of a suspension. Unless indicated otherwise by the context, any directional sequence of the addition of a solution or a suspension to another solution or suspension is possible.

The O-alkylisourea salt of the formula II and the amine of the formula III are preferably employed in a molar ratio of from 2:1 to 1:2, in particular from 1.5:1 to 0.9:1.

The novel reaction normally takes place in an aqueous medium such as water itself or a mixture of water with water-miscible organic solvents such as alcohols, e.g. methanol or ethanol; acetone or THF. The reaction medium normally contains the alcohol $R^5OH$ liberated during the reaction; additional amounts of the alcohol $R^5OH$ can be added where appropriate.

The novel reaction preferably takes place at a pH of from 6 to 14, in particular 8.5 to 12.5, particularly preferably from 9.5 to 12. To maintain a pH in the stated range, it is usually necessary to introduce a base into the reaction medium. Examples of suitable bases are alkali metal hydroxides such as NaOH, in particular as approximately 50% strength solution; KOH, in particular as approximately 50% strength solution; and LiOH, especially as approximately 10% strength solution, and alkaline earth metal hydroxides such as $Ca(OH)_2$. The base to be employed is advantageously selected so that the salt of the cation introduced with the base together with the anion $X^\ominus$ from the O-alkylisourea salt of the formula II shows maximal solubility in the reaction medium. Thus, for example, in cases where $X^\ominus$ is an alkyl sulfate, hydrogen sulfate or one equivalent of sulfate, the use of alkali metal hydroxides is preferred to the use of alkaline earth metal hydroxides.

It is sometimes possible to use mixtures of alkali metal hydroxides whose mixed salts with the $X^\ominus$ anion are more soluble than the purer salts.

The base is preferably introduced as required. This is done by continuously measuring the pH in the reaction medium, comparing the instantaneous pH with a preset pH and adding the amount of base necessary to correct the pH. The measured pH can be provided, for example, in the form of an electronic signal which is compared by an electronic dataprocessor with a preset value and automatically calculates the amount of base required and controls a base-metering system.

The novel process preferably takes place at a temperature of from −20 to 100° C., in particular 0 to 80° C., particularly preferably from 5 to 35° C. The reaction between the O-alkylisourea salt of the formula II and the amine of the formula III is exothermic. To maintain the stated temperature it is therefore usually necessary to cool the reaction medium. This expediently takes place using suitable heat-exchange devices. Alternatively, part of the reaction medium can be continuously circulated by a pump through a temperature-controlled zone. The holdup times in the reactor in the novel process are generally 0.5 to 120, preferably 5 to 72, very particularly preferably 12 to 48 hours.

The novel process can be carried out under elevated pressure, atmospheric pressure or vacuum, e.g. under an absolute pressure down to 10 mbar. Operating under atmospheric pressure is generally preferred. There may be advantages in operating under vacuum since the alcohol $R^5OH$ formed in the reaction and the ammonia which may be formed by side reactions can be continuously removed from the reaction mixture, by which means it is possible to avoid undesired excessive consumption of O-alkylisourea salt. In addition, an evaporative cooling effect can be achieved by operating under vacuum.

The novel process can be carried out batchwise, semicontinuously or continuously, but is preferably carried out continuously. Conventional reactors are suitable for carrying out the novel process continuously, such as, in particular, a continuous stirred vessel reactor or a cascade of stirred vessels. It is expedient to ensure thorough mixing of the reactants in the reaction chamber.

Carrying out the process continuously has the advantage that essentially constant concentrations of the reactants are present in the reaction medium, and an essentially constant amount of dissolved and undissolved guanidine derivative of the formula I is present in the reaction medium. It is possible in this way to maintain an essentially constant, controllable degree of supersaturation and thus a controlled rate of crystallization of the guanidine derivative of the formula I. The control of the rate of crystallization of the guanidine derivative of the formula I makes it possible to obtain products of high purity with substantially uniform particle size distribution and average particle sizes of more than, for example, 100 μm. This makes it possible to reduce the resistance of the suspension on filters for example to less than $10 \times 10^{12}$ mPas.m$^{-2}$, and practicable filtration times are achieved. The resulting crystals are normally sufficiently pure to be used after simple washing and without further purification steps for example as dietary supplements.

In a particularly preferred embodiment, the reaction takes place in a reaction chamber into which O-alkylisourea salt of the formula II and amine of the formula III are continuously introduced and from which crystals of the guanidine derivative of the formula I are continuously removed, preferably in the form of a crystal suspension. The O-alkylisourea salt of the formula II and/or the amine of the formula III are expediently introduced in the form of aqueous solutions. Crystals of the guanidine derivative of the formula I must always be present in the reaction chamber to act as seed crystals for the product formed in the reaction between the newly introduced O-alkylisourea salt and amine. This can be achieved, for example, by controlling the removal of the suspension of crystals of the guanidine derivative of the formula I so that some of the crystals remain in the reaction chamber and serve as seed crystals for further crystallization.

To obtain a product with predictable and uniform size distribution it is preferable to introduce seed crystals of the guanidine derivative of the formula I, preferably in the form of a suspension, continuously into the reaction chamber. The seed crystals introduced in this case may have an average crystal size and/or crystal size distribution different from that of the removed crystals of the guanidine derivative of the formula I.

In a particularly preferred embodiment of this aspect of the invention, the seed crystals added to the reaction chamber are obtained by subjecting the crystals of the guanidine derivative of the formula I removed from the reaction chamber to a size classification to obtain a fine material fraction and a coarse material fraction, and returning the fine material fraction as seed crystals to the reaction chamber and discharging the coarse material fraction as product from the process. The fine material fraction suitable as seed crystals has, for example, a particle size range from 1 to <100 μm. The coarse material fraction has, for example, a particle size range from 100 μm to 500 μm.

The size classification of the crystals can take place both in suspended and in the dry state. For classification in the dry state, the crystals are previously separated from the mother liquor and dried. The fine material fraction obtained, for example, by sieving can be suspended in an aqueous medium for return to the reaction chamber. Examples of suitable devices for size classification are hydrocyclones and wet sieves for classifying suspended crystals and cyclones, sieves or sifters for classifying dried crystals.

The O-alkylisourea salt employed is normally in solid form or in the form of a very viscous oil. It has emerged that when the O-alkylisourea salt is introduced undiluted into the alkaline reaction solution local overheating occurs at the phase boundary between O-alkylisourea salt and reaction medium. The local overheating favors side reactions over the formation of the desired guanidine derivative. If alkyl sulfates are employed as O-alkylisourea salt, the local overheating additionally favors hydrolysis of the alkyl sulfate anion to the sulfate, which results in undesirable excessive consumption of base. The alkali metal and alkaline earth metal sulfates are in addition less soluble than the corresponding alkyl sulfates. In addition, the solid or very viscous O-alkylisourea salt can be mixed into the reaction solution only with difficulty, even with highly effective mixers. The energy input for mixing then sometimes becomes so great that larger crystals of the guanidine derivative of the formula I are destroyed by the action of shear forces. It is therefore preferred to employ the O-alkylisourea salt in the form of an aqueous solution with a content of, normally, 85 to 15, in particular 70 to 30, % by weight.

The aqueous solution in this case normally has a viscosity of from 500 to 1 mPa.s, in particular 100 to 1 mPa.s and particularly preferably 10 to 1 mPa.s. This solution of the O-alkylisourea salt can be made up using an aqueous medium such as water itself. In a preferred aspect of the invention, the aqueous solution of O-alkylisourea salt is prepared using a washing medium resulting from the washing of the resulting crystals of the guanidine derivative of the formula I with an aqueous medium. In this way on the one hand the water consumption in the overall process is minimized, and on the other hand the fraction of guanidine derivative of the formula I which dissolves in the washing medium when the resulting product is washed is returned in the form of the solution of the O-alkylisourea salt to the reaction chamber and is retained in the overall system.

The amine of the formula III can advantageously be employed in the form of an aqueous solution, e.g. with a concentration of from 85 to 15, in particular 70 to 30, % by weight. An example of a suitable solution is a commercially available aqueous solution of sodium sarcosinate with a content of 40% and a purity of 85–90%.

The introduction of the O-alkylisourea salt of the formula II and/or of the amine of the formula III or of the aqueous solutions thereof and, where appropriate, necessary base into the reaction medium can expediently take place by part of the reaction medium being removed from the reaction chamber, being mixed with the O-alkylisourea salt and/or the amine and/or the base, and being returned to the reaction chamber. The removal, the mixing and the return preferably take place continuously, for example by pumping the reaction medium through a metering and mixing zone in which O-alkylisourea salt and/or amine or aqueous solutions thereof and/or base are fed in. It is possible in this way to adjust the concentrations as required. Local concentration peaks and pH variations can be avoided.

The product is removed from the suspension of crystals of the guanidine derivative of the formula I which has been removed as product stream by conventional processes, e.g. by filtration or centrifugation. Suitable devices such as pressure filters, vacuum belt filters, drum filters or centrifuges are known to the skilled worker. Accumulation of impurities present in the O-alkylisourea salt of the formula II employed and/or the amine of the formula III in the system can be prevented by discharging the remaining mother liquor. The mother liquor removed from the system thus serves in particular as discharge stream for the products resulting from the novel process in the form of the alcohol $R^5OH$ and the salt of the cation of the base used with the anion $X^\ominus$.

The crystals removed from the mother liquor can be washed, for example, with cold or hot water. This can be done by suspending the crystals in the washing medium and then removing them again. The washing medium can be used, as mentioned above, for making up the solution of the O-alkylisourea salt and thus be returned to the process.

The crystals of the guanidine derivative of the formula I which have been removed from the mother liquor and washed where appropriate can then be dried by conventional processes. Suitable for this are, for example, an air conveying, pneumatic dryers or fluidized beds. The crystals are expediently dried to a content of moisture which is not bound in the crystal of from 5 to 0% by weight, preferably 2.5 to 0% by weight.

It may be advantageous in the individual case to mix the moist cake of crystals of guanidine derivative of the formula I obtained after removal from the mother liquor with previously dried material and to subject the mixture to further drying in order in this way to avoid caking during the drying. When the process is carried out continuously, this can be achieved by recycling part of the dried material.

Depending on the temperature and ambient humidity, the anhydrous form or a hydrate of the guanidine derivative of the formula I is the most thermodynamically stable form; additional hydrates with differing compositions are obtained where appropriate as metastable structures. In the cases of creatine, the monohydrate is the usual commercial form; during the drying, care must be taken, where appropriate by processes known to the skilled worker, that no unwanted overdrying occurs.

The invention is illustrated in detail by the following examples.

EXAMPLE 1

Batchwise Creatine Synthesis in the Presence of Creatine Crystals

A suspension of 150 g of creatine monohydrate in 150 ml of creatine-saturated water at 15° C. was introduced into a double-wall glass reactor. Over the course of 4 hours, 1.02 kg (3.3 mol) of a 60% strength technical OMI (O-methylisourea) methyl sulfate melt which had been diluted with 500 ml of creatine-saturated water at 15° C. to give an aqueous solution with a viscosity of 3 mPas were metered in. While stirring, the pH was continuously maintained at 11.0 by pumping in a 50% strength aqueous solution of NaOH at 15° C. as required (about 0.24 kg). Synchronously with the metering in of the guanidation agent, 0.825 kg (3 mol) of a 40% strength aqueous solution of sarcosine sodium salt at 15° C. were added; the internal temperature was kept below 20° C. by means of a thermostat. It was possible to stir the suspension without difficulty at all times. Stirring was continued at 15° C. overnight, for a total of 20 hours, and the suspension was forced under a gauge pressure of 1.5 bar through a sintered metal wire cloth composite plate; the resistance in the pressure filter was $3 \times 10^{12}$ mpas $m^{-2}$. The reactor was rinsed with 200 ml of drinking water, and the filter cake was covered with this; the water adhering to the crystals was substantially blown off under a gauge pressure of 0.5 bar. The residue was suspended twice in 325 ml of drinking water each time, stirred vigorously for 30 minutes each time and sucked dry to a residual moisture content of about 10%. Finally, water-saturated air was sucked through the filter cake at room temperature overnight to leave creatine in the form of its monohydrate.

After subtraction of the seed crystals, 299 g (2 mol) of $H_2N$—$C(=NH)$—$NMe$—$CH_2$—$COOH \times H_2O$ remained, which corresponds to a yield of 67% based on sarcosine sodium and 62% based on OMI methyl sulfate. The content of required product can be established by HPLC and titration and was greater than 99.5%, and the sulfated ash was less than 0.1%; the product had an average particle size ($DP_{50}$) of about 150 μm, and no caking occurred while it was being dried.

The following particle size distribution was found by sieve analysis of a sample:

| | |
|---|---|
| >400 μm | 0.1 g |
| >200 μm | 11.4 g |
| >160 μm | 11.9 g |
| >125 μm | 8.8 g |
| >90 μm | 7.9 g |
| >50 μm | 9.2 g |
| <50 μm | 1.0 g |

EXAMPLE 2

Continuous Creatine Synthesis in the Presence of Creatine Crystals

A suspension of 1 g of creatine monohydrate in 150 ml of creatine-saturated water at 15° C. was introduced into a double-wall glass reactor. Then the following two precursor streams (i) and (ii) were metered in continuously and synchronously: (i) 1.15 ml/min of an aqueous solution which had a viscosity of 3 mPas and had been prepared by mixing 730 ml of a 60% strength technical OMI methyl sulfate melt with 650 ml of creatine-saturated water at 15° C. This corresponds to 3.3 mol of precursor for an average holdup time of 20 hours. (ii) 0.56 ml/min of a 40% strength aqueous solution of sarcosine sodium salt at 15° C., which corresponds to 3.0 ml of precursor for an average holdup time of 20 hours. While stirring vigorously, the pH was continuously maintained at 11.0 by pumping in a 50% strength aqueous solution of NaOH at 15° C. as required (about 0.14 ml/min). The internal temperature of the reactor was maintained at 15° C. by a thermostat. As soon as the contents of the flask reached a volume of 2100 ml, each time 100 ml of the product suspension were discharged through a valve. After 100 h (equivalent to 5 times the average holdup time), it can be assumed that a stationary state is reached in the reactor. The suspension with a volume of 2100 ml remaining in the reactor was therefore forced out under a gauge pressure of 1.5 bar through a sintered metal wire cloth composite plate; the resistance in the pressure filter was $3 \times 10^{12}$ mpas $m^{-2}$. The reactor was rinsed with 200 ml of drinking water, and the filter cake was covered with this; the water adhering to the crystals was substantially blown off under a gauge pressure of 0.5 bar. The residue was suspended twice in 325 ml of drinking water each time and vigorously stirred for 30 minutes each time, and sucked dry to a residual moisture content of about 10%. Finally, water-saturated air was sucked through the filter cake at room temperature overnight, leaving creatine in the form of its monohydrate.

246 g (1.65 mol) of $H_2N$—$C(=NH)$—$NMe$—$CH_2$—$COOH \times H_2O$ remained, which corresponds to a yield of 55% based on sarcosine sodium and 50% based on OMI methyl sulfate. The content of required product which can be established by HPLC and titration was greater than 99.5% and the sulfated ash was less than 0.1%; the product had an average particle size of 115 $\mu$m, and no caking occurred during drying thereof.

EXAMPLE 3

Continuous Creatine Synthesis in the Presence of Creatine Crystals in a Reactor Cascade 1 g of creatine monohydrate and 300 ml of creatine-saturated water at a temperature of 15° C. are introduced into a double-wall 2 1 glass reactor with propeller agitator and baffles. Suspension is pumped continuously through a valve in the base at a delivery rate of about 15 l/h through a circuit which has a capacity of about 50 ml and contains a metering and mixing zone and which is provided with a cooling jacket. Over the course of 20 h, 1.3 ml/min of a solution which had previously been mixed from 1530 g (4.95 mol) of OMI methyl sulfate (60%) and 490 ml of creatine-saturated water at a temperature of 5° C. are metered into a metering zone in the direction of flow. With the vigorous mixing, the pH in the mixing zone falls by about 2 to 3 pH steps. Synchronously, 1.4 ml/min of a solution which is at room temperature and which had been mixed from 1240 g (4.5 mol) of sarcosine NA salt (40% in water; pH=14), 200 ml of sodium hydroxide solution (50%) and 490 ml of creatine-saturated water are metered into the metering zone downstream from the place where the OMI methyl sulfate is metered in. With the vigorous mixing, the pH in the mixing zone rises by about 1 to 2 pH steps.

A pH of 11.0 was maintained in the glass reactor by metering in 50% strength NaOH through a micrometering pump as required. The temperature of the reactor is limited to 15° C. by a thermostat; the agitator rotates at about 300 rpm. The cooling in the circuit is adjusted so that the suspension which is pumped round emerges at a temperature of 15° C. at the end of the metering zone.

As soon as the volume of liquid in the reactor reaches 1050 ml, product suspension is discharged from the circuit through a pneumatically controlled valve upstream of the inlet into the metering zone into a double-wall 2 1 glass reactor which has a propeller agitator and into which 250 ml of creatine-saturated water at a temperature of 15° C. have been introduced. The pH in this reactor is also maintained at 11 by metering in 50% strength NaOH as required. As soon as the volume of liquid in the second reactor reaches 1050 ml, product suspension is discharged through a pneumatically controlled valve in the base into a double-wall 2 l glass reactor which is located underneath and has a propeller agitator, into which 100 ml of creatine-saturated water at a temperature of 15° C. has been introduced. When the volume reaches 1050 ml, the product suspension is discharged through an overflow.

The total holdup time over the three reactors in this arrangement is 20 h. The above meterings are continued for a further nine holdup times (180 h). In each holdup time, 3150 ml of free-flowing product suspension with a solids content of about 15% are produced and are taken off continuously at 25° C. through a sintered glass funnel.

Immediately after the metering is complete, the contents of the third reactor are forced out through a pressure filter with a sintered metal base. The reactor is rinsed with 100 ml of drinking water at a temperature of 20° C., which is used to cover the material on the filter. Air is then used to blow dry for 10 min until the residual moisture content is 20%. The residue is then suspended twice with a portion of 160 ml of drinking water at a temperature of 20° C. each time in the pressure filter, stirred vigorously for 30 min and sucked dry. Air with the ambient moisture content is sucked through the resulting moist crude products at room temperature overnight. 156.5 g of pure white crystals of creatine monohydrate remain, corresponding to a yield of 70% based on sarcosine Na salt.

The yield can be further optimized by altering the process parameters such as, in particular, the holdup time.

COMPARATIVE EXAMPLE 0.3 kg (1 mol) of a 37% strength technical aqueous solution of sodium sarcosinate was introduced into a double-wall glass reactor. It was vigorously stirred and the pH was continuously maintained at 11.0 by adding a 37% strength aqueous solution of NaOH as required. Then 0.465 kg (1.5 mol) of 60% strength O-methylisourea methyl sulfate (viscosity 3000 mPas) was added, starting at 15° C., at a rate (approximately over the course of 4 hours) such that the macroscopically measurable internal temperature did not exceed 20° C. As a result of the poor miscibility, considerable schlieren formation is evident (O-methylisourea methyl sulfate has a pH below 1 in a 1:1 dilution with water), and stirring of the contents of the mixture became increasingly difficult as product formation increased. After about 1 h, crystallization of creatine started. The amount of creatine in solution, which can be established by HPLC at times exceeded the saturation concentration five-fold. Stirring was continued at room temperature overnight, and the suspension was forced with a gauge pressure of 1.5 bar through a sintered metal wire cloth composite plate; the resistance on the filter as $8 \times 10^{15}$ mpas m$^{-2}$. It was possible to remove only incompletely the NaOSO$_2$OMe, part of which had also precipitated, and the Na$_2$SO$_4 \times$10H$_2$O formed by hydrolysis, by washing with 0.12 l of water and 0.1 l of methanol. Drying of the residue at room temperature and normal humidity gives crude creatine monohydrate weighing 0.1 kg (65% yield based on sodium sarcosinate, 43% based on OMI) and having a sulfated ash of 3%. The product caked to hard aggregates on drying, and the average particle size of the crystallites was 30 μm, with a very broad distribution, which led to extensive dust development on working with the product further.

We claim:

1. A process for preparing guanidine derivatives of the formula I

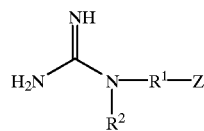

in which

R$^1$ is C$_1$–C$_8$-alkylene or a divalent cycloaliphatic radical with 5 to 10 carbon atoms R$^2$ is H, C$_1$–C$_8$-alkyl, or R$^1$ and R$^2$ represent, together with the N atom to which they are bonded, a 5- or 6-membered Z-substituted ring, Z is COOR$^3$, SO$_2$OR$^3$ or PO(OR$^3$)(OR$^4$), R$^3$ is in each case independently H, an alkali metal or an equivalent of an alkaline earth metal and R$^4$ is in each case independently H, an alkali metal, an equivalent of an alkaline earth metal or C$_1$–C$_6$-alkyl, which process comprises providing seed crystals of the guanidine derivative of the formula I and reacting an O-alkylisourea salt of the formula II

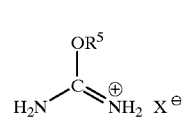

in which R$^5$ is C$_1$–C$_8$-alkyl and X$^\ominus$ is an equivalent of an anion, with an amine of the formula III

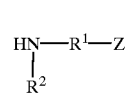

in the presence of the seed crystals.

2. A process as claimed in claim 1, comprising continuously introducing into a reaction chamber an O-alkylisourea salt of the formula II and an amine of the formula III and continuously removing from the reaction chamber crystals of the guanidine derivative of the formula I.

3. A process as claimed in claim 2, wherein seed crystals of the guanidine derivative of the formula I are continuously introduced into the reaction chamber.

4. A process as claimed in claim 3, wherein the removed crystals are subjected to a size classification to result in a fine material fraction and a coarse material fraction, and the fine material fraction is returned as seed crystals to the reaction chamber, and the coarse material fraction is discharged from the process as product.

5. A process as claimed in claim 1, wherein the O-alkylisourea salt is employed in the form of an aqueous solution with a viscosity of from 1 to 500 mPa.s.

6. A process as claimed in claim 5, wherein the resulting crystals of the guanidine derivative of the formula I are washed with an aqueous medium, and the washing medium is wholly or partly used to prepare the aqueous solution of the O-alkylisourea salt.

7. A process as claimed in claim 1, wherein the reaction takes place at a pH of from 6 to 14.

8. A process as claimed in claim 1, wherein the reaction takes place at a temperature of from –20 to 100° C.

9. A process as claimed in claim 1, wherein the reaction takes place in the presence of from 1 to 40% by weight of the seed crystals based on the reaction mixture.

10. A process as claimed in claim 1 for preparing creatine, wherein the amine of the formula III is sodium or potassium sarcosinate.

* * * * *

UNITED STATES PATENT AND TRADEMARK OFFICE
CERTIFICATE OF CORRECTION

PATENT NO.: 6,143,929

DATED: November 7, 2000

INVENTOR(S): KESSEL et al.

It is certified that error appears in the above-identified patent and that said Letters Patent is hereby corrected as shown below:

Col. 1, line 18, "$H_1-C_8$-alkyl" should be --H, $C_1-C_8$-alkyl--.

Col. 2, line 11, 97%. in" should be --97%. In--.

Col. 8, line 55 (third line of the table), "11.9 g" should be --11.0 g--.

Col. 9, line 24, "mpas" should be --mPas--.

Col. 11, line 6, "mpas" should be --mPas--.

Signed and Sealed this

First Day of May, 2001

Attest:

NICHOLAS P. GODICI

*Attesting Officer*    *Acting Director of the United States Patent and Trademark Office*